United States Patent [19]

Kobayashi et al.

[11] 4,451,569

[45] May 29, 1984

[54] STABLE ENZYME COMPOSITION

[75] Inventors: Setsuo Kobayashi; Kazuo Beppu; Hiroshi Shimizu; Satoshi Ogawa, all of Otsu; Ryotaro Kotani, Moriyama, all of Japan

[73] Assignee: Toyo Boseki Kabushiki Kaisha, Osaka, Japan

[21] Appl. No.: 394,165

[22] Filed: Jul. 1, 1982

[30] Foreign Application Priority Data

Jul. 6, 1981 [JP]  Japan .............................. 56-106130

[51] Int. Cl.$^3$ .......................... C12N 9/96; C12N 9/08
[52] U.S. Cl. ...................................... 435/188; 435/192
[58] Field of Search ................................ 435/188, 192

[56] References Cited

U.S. PATENT DOCUMENTS 3,133,001  5/1964  Muset .............................. 435/192 X

OTHER PUBLICATIONS

Nakamura et al., Biochimica et Biophysica Acta 358 (1974) 251-261.
Biochemistry vol. 13, pp. 1825-1828 (1974).

*Primary Examiner*—Lionel M. Shapiro
*Attorney, Agent, or Firm*—Wenderoth, Lind & Ponack

[57] ABSTRACT

There is provided a stable enzyme composition comprising glutathione peroxidase and at least one stabilizer compound selected from the group consisting of pentoses, hexoses, penthahydric sugar alcohols, hexahydric sugar alcohols and disaccharides.

8 Claims, No Drawings

STABLE ENZYME COMPOSITION

The present invention relates to a stable composition of glutathione peroxidase (Glutathione: hydrogen peroxide oxidoreduclase, EC 1. 11. 1.9).

Glutathione peroxidase was derived from bovine erythrocytes by Mills in 1957 [J. Biol. Chem., 229, 189 (1957)], and is known as a metalloenzyme containing selenium. This enzyme catalyzes the reaction shown by the following formula (L), and also, even when hydrogen peroxide in the formula (1) is replaced with t-butyl hydroperoxide, cumene hydroperoxide, lauryl hydroperoxide or progesterone-17-α-hydroperoxide, it will easily decompose these peroxides in the presence of reduction type glutathione.

$$2GSH + H_2O_2 \rightarrow GSSG + 2H_2O \tag{1}$$

GSH: Reduction type glutathione
GSSG: Oxidation type glutathione

Said enzyme is obtained from the organs such as erythrocytes, liver, crystalline lens, etc. of various animals (man, cow, sheep, rat, pig, etc.), and the method for its purification is already well known. For example, there are some methods reported by S. H. Oh et al. [Biochemistry, 13, 1825 (1974)], Nakamura et al. [Biochem. Biophys. Acta, 358, 251 (1974)], Yagi et al. [The Proceedings on the 52nd Meeting of Biochemical Society of Japan, 723 (1979)] and the like. Relating to a storage and stabilization method for the purified enzyme, methods such as storage in phosphate buffers (pH, 7.0), storage in ethanol solution, freeze storage in the presence of a reducing agent (e.g. glutathione, dithiothreitol) and the like are known. These known stabilization methods are limited to the stabilization of said enzyme for up to three months. And the glutathione peroxidase preserved by methods other than freeze storage in the presence of a reducing agent retains its activity at only 60 to 80% (reference is an activity value just before storage) after one month cold storage. The freeze storage in the presence of a reducing agent shows an activity retention of about 90% after three months storage, but such method has various disadvantages such that freezing is necessary for storage, and transportation of the frozen preparation is not easy.

We have conducted research to find a new method which is superior in stability to the known methods and requires no freeze storage, and as a result, have found that, when a sugar or sugar alcohol is added to said enzyme as a stabilizer, an enzyme composition much superior in stability as compared with the prior-art stabilized compositions can be obtained.

According to the present invention, there is provided a stable enzyme composition comprising glutathione peroxidase and one or more compounds selected from the group consisting of pentoses, hexoses, pentahydric sugar alcohols, hexahydric sugar alcohols and disaccharides.

In the present invention, glutathione peroxidase, when added with the foregoing stabilizer, becomes extremely superior in stability and superior in storage stability as compared with the use of conventional stabilizers.

Glutathione peroxidase used in the present invention may be from any source and not limited to those which are obtained from the organs such as erythrocytes, liver, crystalline lens, etc. of various animals (e.g. man, cow, sheep, rat, pig, etc.).

The pentoses used in the present invention include for example D-, L-arabinose, D-, L-xylose, D-, L-lyxose, D-ribose, D-, L-xylulose, D-, L-ligrose and the like.

The hexoses include for example D-, L-galactose, D-glucose, D-mannose, D-sorbose, D-fructose and the like.

The pentahydric sugar alcohols used in the present invention include for example D-arabitol, xylitol and the like.

The hexahydric sugar alcohols include for example galactitol, D-sorbitol, D-mannitol and the like.

Further, the disaccharides include for example xylobiose, maltose, isomaltose, laminaribiose, cellobiose, gentiobiose, lactose, sucrose and the like.

The amount of stabilizer used in the present invention is equal to or more than the protein weight of glutathione peroxidase, preferably 1 to 10 times the protein weight.

As a method for mixing the enzyme and the stabilizer, there may be employed any proper method, for example a method in which a buffer solution containing dissolved enzyme is mixed with a solution containing the foregoing stabilizer dissolved; a method in which the enzyme and the stabilizer are mixed in a buffer solution; and a method in which the enzyme is mixed with a solution containing dissolved stabilizer. Solutions containing the enzyme and stabilizer may be stored as they are or in freeze drying. Freeze drying may be carried out as usual.

The stabilized glutathione peroxidase composition obtained in the present invention is superior in stability as compared with those in the known methods, showing an activity retention of not less than about 80% even after six months storage. Further, there is no need for freezing during storage, and the activity retention is not affected by temperature, if the enzyme is stored at a temperature not higher than 20° C.

In this invention, measurement of enzyme activity was conducted as follows: Using 2 ml of a 50 mM phosphate buffer solution (pH 7.0) containing 2 mM EDTA, 1 mM glutathione, 1 mM sodium azide, 0.16 mM NADPH, 0.4 mM hydrogen peroxide, 0.14 unit glutathione reductase and 0.01 unit glutathione peroxidase, the absorbance at 340 nm of the solution was recorded at 25° C. for 3 minutes on a spectrophotometer, and a change in absorbance per minute was obtained from the linear portion. The blank value was obtained by using water in place of the enzyme solution.

As for the unit of glutathione peroxidase, the amount of the enzyme necessary to decompose 0.5 μmole of NADPH in one minute under the foregoing reaction condition was taken as one unit.

The invention will be further explained in the following Examples which are given for illustration only and not for limiting the scope of the invention.

EXAMPLE 1

From bovine blood, glutathione peroxidase was purified according to the method of Yagi et al. [The gist of the lectures at the 52nd Meeting of Biochemical Society of Japan, 723 (1979)]. Thus, 10 liters of the bovine blood (sodium citrate was added as anti-coagulant) was centrifuged to remove the plasma fraction, and after washing with a physiological saline water, about 5 liters of erythrocyte was obtained by centrifugation. The erythrocyte obtained (5 liters) was hemolyzed with addition of 2.5 liters of distilled water, and then 2.625 liters of carbon tetrachloride and 5.85 liters of ethanol were added with stirring to modify and deposit hemoglobin. Thereafter, 7.5 liters of distilled water was added, and about 15 liters of the supernatant liquor was separated by centrifugation. From the supernatant liquor obtained, glutathione peroxidase could be separated in a yield of about 20% by applying column chromatography with DEAE Sephadex A-50, Sephacryl S-200, Activated thiol 4B and Sephadex G-150.

A 50 mM phosphate buffer solution (pH 7.0) of the glutathione peroxidase obtained was concentrated to a protein concentration of 10 mg/ml using a ultrafilter (Toyo Kagaku Sangyo K.K.). To the phosphate buffer solution containing said enzyme was added each of the substances under the condition shown in Table 1, followed by freeze drying. The activity retention after storage for the required period of time is shown in Table 1.

TABLE 1

| | Stabilizer | Addition ratio*2 | Activity retention (%)*1 | | | |
|---|---|---|---|---|---|---|
| | | | 0 day | 1 month | 3 months | 6 months |
| Present invention | Arabinose | 1 | 92 | 92 | 90 | 87 |
| | Glucose | 1 | 94 | 92 | 89 | 84 |
| | Xylitol | 1 | 95 | 92 | 90 | 85 |
| | Sorbitol | 1 | 95 | 92 | 90 | 88 |
| | Sucrose | 1 | 97 | 95 | 95 | 93 |
| Comparative example | Erythrose | 1 | 69 | 65 | 60 | 52 |
| | Heptulose | 1 | 63 | 60 | 55 | 48 |
| | Erythritol | 1 | 60 | 51 | 48 | 40 |
| | Sedoheptitol | 1 | 65 | 58 | 52 | 39 |
| | Amylose | 1 | 70 | 65 | 50 | 35 |
| | No addition | — | 50 | 30 | 27 | 20 |

*1Storage was carried out at 4° C. The activity retention was calculated with the activity value before freeze drying as 100%.
*2Weight of added substance/weight of said enzyme protein.

EXAMPLE 2

Glutathione peroxidase obtained in the same manner as in Example 1 was similarly concentrated to a protein concentration of 10 mg/ml using ultrafilter, and the stabilizer shown in Table 2 was added at various addition ratios, followed by freeze drying. The results are shown in Table 2.

TABLE 2

| Stabilizer | Addition ratio | Activity retention (%) | |
|---|---|---|---|
| | | 3 months | 6 months |
| Arabinose | 4 | 92 | 87 |
| | 1 | 91 | 87 |
| | 0.5 | 79 | 65 |
| Glucose | 4 | 90 | 85 |
| | 1 | 90 | 84 |
| | 0.5 | 77 | 63 |
| Xylitol | 4 | 91 | 86 |
| | 1 | 89 | 85 |
| | 0.5 | 78 | 66 |
| Sorbitol | 4 | 91 | 88 |
| | 1 | 91 | 87 |
| | 0.5 | 75 | 61 |
| Sucrose | 4 | 95 | 94 |
| | 1 | 96 | 93 |
| | 0.5 | 79 | 68 |

Storage was carried out at 4° C.

EXAMPLE 3

Glutathione peroxidase obtained in the same manner as in Example 1 was similarly concentrated (to a protein concentration of 10 mg/ml) using a ultrafilter, and the stabilizer was added thereto in an amount equivalent (addition ratio, 1) to the protein weight. The mixture was freeze-dried and stored at a temperature shown in Table 3.

TABLE 3

| Stabilizer | Storage temperature (°C.) | Activity retention (%) | |
|---|---|---|---|
| | | 3 months | 6 months |
| Arabinose | 30 | 71 | 61 |
| | 20 | 90 | 84 |
| | 4 | 91 | 86 |
| Glucose | 30 | 69 | 59 |
| | 20 | 87 | 83 |
| | 4 | 90 | 85 |
| Xylitol | 30 | 73 | 62 |
| | 20 | 89 | 83 |
| | 4 | 90 | 85 |
| Sorbitol | 30 | 72 | 60 |
| | 20 | 90 | 86 |
| | 4 | 91 | 88 |
| Sucrose | 30 | 71 | 60 |
| | 20 | 95 | 92 |
| | 4 | 96 | 94 |

COMPARATIVE EXAMPLE 1

Glutathione peroxidase obtained in the same manner as in Example 1 was similarly concentrated using a ultrafilter to obtain a 25 mM phosphate buffer solution (pH 7.0) having a protein concentration of 10 mg/ml. To this phosphate buffer solution was added each of the stabilizers described below in an amount of 1/250 per weight of enzyme protein. The enzyme activity retention of the resulting solution is shown in Table 4. Also, an enzyme activity retention when ethanol was added to this phosphate buffer to be 24% of ethanol solution is shown together.

TABLE 4

| Stabilizer | Activity retention (%) | | | |
|---|---|---|---|---|
| | 0 day | 1 month | 3 months | 6 months |
| None | 100 | 65 | 40 | 35 |
| Glutathione | 100 | 70 | 60 | 49 |
| Dithiothreitol | 100 | 98 | 80 | 59 |
| Glutathione + dithiothreitol | 100 | 98 | 90 | 60 |
| 24% Ethanol solution | 100 | 98 | 80 | 40 |

What we claim is:
1. A stable enzyme composition in freeze-dried form comprising glutathione peroxidase and at least one stabilizer compound selected from the group consisting of pentoses, hexoses, pentahydric sugar alcohols, hexahydric sugar alcohols and disaccharides.
2. The composition as claimed in claim 1 wherein the pentoses are D-, L-arabinose, D-L-xylose, D-, L-lyxose, D-ribose, D-, 1*xylulose and D-, L-ligrose.
3. The composition as claimed in claim 1 wherein the hexoses are D-, L-galactose, D-glucose, D-mannose, D-sorbose and D-fructose.
4. The composition as claimed in claim 1 wherein the pentahydric sugar alcohols are D-arabitol and xylitol.
5. The composition as claimed in claim 1 wherein the hexahydric sugar alcohols are galactitol, D-sorbitol and D-mannitol.
6. The composition as claimed in claim 1 wherein the disaccharides are xylobiose, maltose, isomaltose, laminaribiose, cellobiose, gentiobiose, lactose and sucrose.
7. The composition as claimed in any of the preceding claims, wherein the amount of the stabilizer compound is at least equal to the protein weight of glutathione peroxidase.
8. The composition as claimed in claim 7 wherein the amount of the stabilizer compound is 1 to 10 times the protein weight of glutathione peroxidase.

* * * * *